United States Patent [19]

Fujikura et al.

[11] Patent Number: 4,602,107

[45] Date of Patent: Jul. 22, 1986

[54] PROCESS FOR PRODUCING TRYCYCLO[5.2.1.0$^{2,6}$]DECANE-2-CARBOXYLIC ACID

[75] Inventors: Yoshiaki Fujikura, Ichikaimachi; Naotake Takaishi; Yoshiaki Inamoto, both of Utsunomiya, all of Japan

[73] Assignee: Kao Corporation, Tokyo, Japan

[21] Appl. No.: 515,022

[22] Filed: Jul. 18, 1983

[30] Foreign Application Priority Data

Jul. 22, 1982 [JP] Japan ............................... 57-128235

[51] Int. Cl.$^4$ ..................... C07C 51/09; C07C 61/12
[52] U.S. Cl. .................................................. 562/499
[58] Field of Search ........................................ 562/499

[56] References Cited

U.S. PATENT DOCUMENTS 4,374,052  2/1983  Fujikura et al. ................. 252/522 R
4,411,828 10/1983  Fujikura et al. .................... 560/117

FOREIGN PATENT DOCUMENTS 2019841  7/1979  United Kingdom .

OTHER PUBLICATIONS

*Justus Liebigs Ann. Chem.*, Bd. 638, pp. 111–121 (1960), Koch et al.

*Primary Examiner*—Natalie Trousof
*Assistant Examiner*—Patricia M. Scott
*Attorney, Agent, or Firm*—Oblon, Fisher, Spivak, McClelland & Maier

[57] ABSTRACT

An advantageous process for producing tricyclo[5.2.1.0$^{2,6}$]decane-2-carboxylic acid which is useful as a perfume composition.

According to the invention, tricyclo[5.2.1.0$^{2,6}$]dec-8-yl formate (II) is contacted with an inorganic strongly acidic catalyst to obtain tricyclo[5.2.1.0$^{2,6}$]decane-2-carboxylic acid (I).

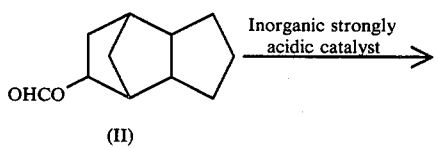

(II)

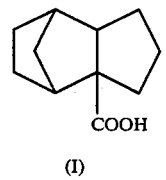

(I)

3 Claims, No Drawings

PROCESS FOR PRODUCING TRYCYCLO[5.2.1.0$^{2,6}$]DECANE-2-CARBOXYLIC ACID

BACKGROUND OF THE INVENTION (i) Field of the Invention:

This invention relates to a process for producing tricyclo[5.2.1.0$^{2,6}$]decane-2-carboxylic acid which belongs to tricyclo carboxylic acids.

(ii) Description of the Prior Art:

Tricyclo[5.2.1.0$^{2,6}$]decane-2-carboxylic acid is a known compound (refer to H. Koch et al, Liebigs Ann. Chem., 638, 111 (1960)), and it has been reported that ester derivatives and alcohol derivatives derived therefrom are very much useful as perfumes (refer to Japanese Patent Application Laid-Open No. 128735/1981).

Heretofore, the tricyclo[5.2.1.0$^{2,6}$]decane-2 -carboxylic acid (I) has been produced by reacting 8-hydroxytricyclo[5.2.1.0$^{2,6}$]decane (III) with carbon monoxide and water, or with formic acid in the presence of sulfuric acid to carboxylate the 2-position thereof.

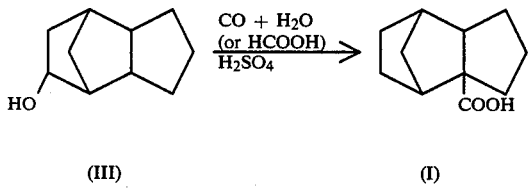

(III)  (I)

Such a carboxylating reaction is generally referred to as Koch reactions, among which a method of reacting an alcohol or olefin with carbon monoxide and water in the presence of an inorganic strongly acidic catalyst is referred to as the CO pressure method, and a method of reacting formic acid is referred to as the formic acid method.

However, these known Koch reactions are not completely satisfactory as the process for producing tricyclo[5.2.1.0$^{2,6}$]decane-2-carboxylic acid since they have the following defects. Specifically, the CO pressure method involves drawbacks in that (1) since it is important to increase the pressure of carbon monoxide (CO) for suppressing the formation of tars in order to improve the yield, it is required to use a pressure-proof vessel, which means a restriction in view of the facility; (2) it requires energy for pressurizing the carbon monoxide; and (3) since the reaction is carried out in the presence of a water-containing acid catalyst, special materials are required for the autoclave, which causes an increase in the installation cost. The formic acid method, although being free from the drawbacks as in the CO pressure method since the reaction can be taken place under ambient pressure, involves several drawbacks in that (1) the yield will be decreased unless formic acid is used in a large excess to the alcohol or olefin; (2) the excess formic acid in the reaction system is decomposed by the acid into water and carbon monoxide, with the resulting water reducing the catalyst activity, and the carbon monoxide being discharged as a gas to cause in undesired circumstantial problems; (3) since the excess formic acid can not be recovered, it results in disadvantages in view of the cost; and (4) since formic acid is often less miscible with olefins and alcohols, it requires to introduce the formic acid and the reaction substrate at an accurate dropping rate to the reaction system for preventing the decrease in the yield, which renders the procedures much complicated.

Further, one of the problems involved throughout the Koch reactions is that acid has to be used in an extremely large amount. Since the acid can not be always recovered depending on the case, the disposition for the great amount of wasted acid provides a significant problem in view of the production step. Even if the acid can be recovered, the use of such great amount of acid inevitably leads to the disadvantage of decreasing the charge amount per one reaction cycle.

SUMMARY OF THE INVENTION

In view of the foregoing present status, the inventors of the present application have made an earnest study for the advantageous process for producing tricyclo[5.2.1.0$^{2,6}$]decane-2-carboxylic acid and, as a result, have accomplished this invention on the basis of the discovery that the aimed compound can be obtained while eliminating the defects in the prior art process, with much convenience and at a good yield by contacting tricyclo[5.2.1.0$^{2,6}$]dec-8-yl formate (II) with an inorganic strongly acidic catalyst in accordance with the following reaction scheme:

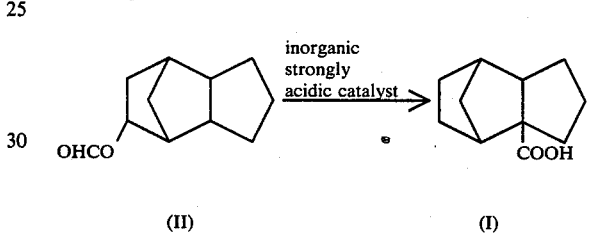

(II)  (I)

DETAILED DESCRIPTION OF THE INVENTION AND PREFERRED EMBODIMENTS

The tricyclo[5.2.1.0$^{2,6}$]dec-8-yl formate (II) as the starting material in this invention may have the formyloxy group and 3, 4, 5-position trimethylene groups either at the exo- or endo- position and it can be produced by reacting a corresponding alcohol or olefin with formic acid in any one of known methods. Examples of such known methods include (1) a method of reacting an alcohol with formic acid in admixture, or reacting the liquid mixture of them with a minor amount of acid such as a concentrated sulfuric acid, aryl sulfonic acid and boron trifluoride-ether complex and (2) a method of reacting the liquid mixture of an olefin and formic acid under heating and agitation, or reacting the liquid mixture with incorporation of a minor amount of an acid catalyst such as perchloric acid. However, any method can be utilized as the production process for the compound (II) so long as it gives esterification with formic acid.

The inorganic strongly acidic catalyst usable herein includes known catalysts employed in Koch reactions, for example, concentrated sulfuric acid (at a concentration higher than 80%), phosphoric acid, hydrofluoric acid, boron trifluoride-phosphoric acid, boron trifluoride hydrate, boron trifluoride-methanol, as well as mixtures thereof. In the process according to the invention, the reaction occurs even with the use of a small amount of the acid catalyst, and an increase in the amount of the acid leads to the improvement in the yield. Accordingly, the amount of the inorganic strongly acidic catalyst employed, while varying depending on the type of the catalyst, is preferably between 0.5–24 mols per one mol of the formic acid ester (I) in the case of using concentrated sulfuric acid (95%) and the amount is, preferably, less than 6 mol when taking the disposal of the wasted acid further into consideration.

The reaction temperature, while varying depending on the type of the acid catalyst, is preferably between 0–80° C. If the reaction temperature is lower than 0° C., the reaction rate is very slow and the yield is reduced. While on the other hand, at a temperature higher than 80° C., the formation of tars is increased to provide economical disadvantages.

In the process according to this invention, while the reaction may be proceeded even in the absence of a reaction solvent, the reaction can also be taken place in the presence of such solvent as not interfering the reaction of this invention, for example, straight-alkanes such as n-pentane and n-hexane; or halogenated solvent such as carbon tetrachloride.

Although it is not usually required to pressurize the carbon monoxide, pressurization is effective in the case more improved reaction yield or more decreased amount of acid employed are desired. In such a case, since no substantial improvement can be expected with the pressure of the carbon monoxide up to about 5 atm, it is necessary to pressurize the medium to above 5 atm.

This invention will now be explained in more detail referring to the following examples.

EXAMPLE 1

Synthesis for tricyclo[5.2.1.0$^{2,6}$]decane-2-carboxylic acid:

588 g (6 mol) of 95% concentrated sulfuric acid were stirred at a temperature of 30° C., to which were added 180 g (1 mol) of tricyclo[5.2.1.0$^{2,6}$]dec-8-yl formate over 2 hours (refer to literature, F. Bergmann and H. Japhe, J. Amer. Chem. Soc. 1826 (1947)). After the completion of the addition, they were continuously stirred at the same temperature for 30 min. After the reaction was over, they were poured into 400 g of ice and water and then extracted with chloroform. After washing the extract with saturated saline water, it was dried over anhydrous magnesium sulfate. After filtration, the solvent was distilled off and the residue was subjected to distillation to obtain 130 g of the above-mentioned carboxylic acid product (72.2% yield). The product was a mixture of two isomers, that is, exo-tricyclo[5.2.1.0$^{2,6}$]-decane-endo-2-carboxylic acid (45%) and endo-tricyclo [5.2.1.0$^{2,6}$]decane-exo-2-carboxylic acid (55%).

It was confirmed that both of the products were completely identical with the standard products synthesized according to the literature (H. Koch and W. Haaf, Liebigs Ann. Chem. 638, 111 (1960)) with respect to gas chromatographic retention time and also to IR spectrum for each of the isomers upon gas chromatographic separation.

EXAMPLE 2

The reaction was carried out under the same conditions as in Example 1 except that the amount of the sulfuric acid employed was varied as shown in Table 1, to examine the yield of tricyclo[5.2.1.0$^{2,6}$]decane-2-carboxylic acid. The results are shown in Table 1.

Table 1 indicates that good yield can be obtained in the process according to this invention even with the use of a small amount of the acid. As the amount of the acid employed increases, it leads to the improvement in the yield.

TABLE 1

| Starting material | Sulfuric acid (mol) | Yield (%) |
|---|---|---|
| OCHO— (structure) (1 mol) | 6 | 72.2 |
| | 8 | 74.1 |
| | 16 | 79.5 |
| | 24 | 81.2 |

EXAMPLE 3

The reaction was carried out in the same manner as in Example 1 in an autoclave except using pressurized carbon monoxide as the reaction system and that the pressure for the carbon monoxide and the amount of the sulfuric acid were varied as shown in Table 2, to examine the yield for tricyclo[5.2.1.0$^{2,6}$]decane-2-carboxylic acid. The results are shown in Table 2.

Although good yield can be obtained without using carbon monoxide and under the condition of using a small amount of the acid in the process according to this invention, the yield can further be improved by pressurizing the carbon monoxide as shown in Table 2.

TABLE 2

| Starting material | Sulfuric acid (mol) | CO Pressure (atom) | Yield (%) |
|---|---|---|---|
| OCHO— (structure) (1 mol) | 6 | 0 | 72.2 |
| | 6 | 10 | 77.6 |
| | 6 | 20 | 91.0 |
| | 4 | 20 | 88.6 |
| | 2 | 50 | 76.1 |
| | 1 | 50 | 67.5 |

COMPARATIVE EXAMPLE 1

Synthesis for exo-tricyclo[5.2.1.0$^{2,6}$]decane-endo-2-carboxylic acid (refer to the Japanese translation for experimental examples, by H. Koch, et al., Liebigs Ann. Chem., 638, 111 (1960))

152 g (1 mol) of 8-exo-hydroxy-endo-tricyclo [5.2.1.0$^{2,6}$]decane, 276 g (6 mol) of formic acid and 1570 g (16 mol) of 99% concentrated sulfuric acid were reacted at a temperature between 10–14° C. After the reaction was over, they were neutralized with an alkali and subjected to distillation to obtain 140 g of solid exo-tricyclo-[5.2.1.0$^{2,6}$]decane-endo-2-carboxylic acid (78% yield).

boiling point: 170–177° C./13 mmHg

REFERENCE EXAMPLE 1

Synthesis for tricyclo[5.2.1.0$^{2,6}$]dec-8-yl formate

A liquid mixture comprising 1020 g (7.7 mol) of dicyclopentadiene and 1063 g (23.1 mol) of 99% formic acid was stirred at 100° C. for 24 hours. Formic acid was recovered through distillation and the residue was further subjected to distillation under a reduced pressure to obtain 1213 g of an unsaturated formic acid ester, that is, tricyclo[5.2.1.0$^{2,6}$]dec-3-ene-8-yl formate (84% yield, b.p. 120–125° C./17 mmHg).

600 g (3.3 mol) of the above-obtained unsaturated formic acid ester and 12 g of 5% palladium-activated carbon were charged in a 1 liter autoclave and reacted at an initial hydrogen pressure of 100 atm and reaction temperature of 80° C. till the hydrogen absorption was observed no more. After the reaction was over, the catalyst was removed through filtration and the organic phase was distilled to obtain 582 g of a saturated formic acid ester that is, tricyclo[5.2.1.0$^{2,6}$]dec-8-yl-formate (96% yield). boiling point: 120–123° C./14 mmHg.

(Note)

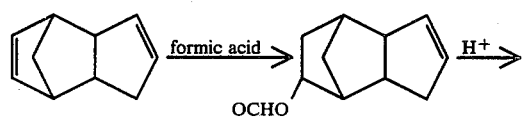

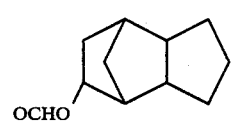

What is claimed is:

1. A process for producing tricyclo-[5.2.1.0$^{2,6}$]dec-ane-2-carboxylic acid of the formula

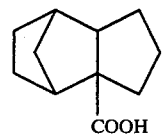   (I)

wherein tricylco[5.2.1.0$^{2,6}$]dec-8-yl formate represented by the formula (II):

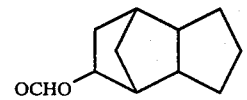

is contacted with an inorganic strongly acidic catalyst which is at least one member selected from the group consisting of sulfuric acid, phosphoric acid, hydrofluoric acid, boron trifluoride-phosphoric acid, boron trifluoride hydrate, boron trifluoride-methanol and mixture thereof.

2. The process of claim 1, wherein the said inorganic strongly acidic catalyst is concentrated sulfuric acid.

3. The process of claim 1, wherein the carbon monoxide under pressure is used in the reaction system.

* * * * *